(12) United States Patent
Spala

(10) Patent No.: US 12,103,908 B2
(45) Date of Patent: Oct. 1, 2024

(54) DISTILLATION PROCESS FOR PRODUCING A LOW TPP PHENATE

(71) Applicant: CHEVRON ORONITE COMPANY LLC, San Ramon, CA (US)

(72) Inventor: Eugene Edward Spala, Fairfield, CA (US)

(73) Assignee: CHEVRON ORONITE COMPANY LLC, San Ramon, CA (US)

( * ) Notice: Subject to any disclaimer, the term of this patent is extended or adjusted under 35 U.S.C. 154(b) by 0 days.

(21) Appl. No.: 16/815,062

(22) Filed: Mar. 11, 2020

(65) Prior Publication Data

US 2020/0299233 A1 Sep. 24, 2020

Related U.S. Application Data

(60) Provisional application No. 62/820,612, filed on Mar. 19, 2019.

(51) Int. Cl.
| | | |
|---|---|---|
| C07C 319/28 | (2006.01) | |
| B01D 3/40 | (2006.01) | |
| C10M 135/06 | (2006.01) | |
| C07C 323/20 | (2006.01) | |
| C10N 10/04 | (2006.01) | |
| C10N 30/04 | (2006.01) | |

(52) U.S. Cl.
CPC .............. *C07C 319/28* (2013.01); *B01D 3/40* (2013.01); *C10M 135/06* (2013.01); *C07C 323/20* (2013.01); *C10M 2219/088* (2013.01); *C10N 2010/04* (2013.01); *C10N 2030/04* (2013.01)

(58) Field of Classification Search
CPC .......................... C10M 135/28; C10M 135/06; C10M 135/02; C10M 177/00; C10M 2219/02; C10M 2219/088; C10N 2070/02; C10N 2030/40; C10N 2070/00; C10N 2030/04; C10N 2010/04; C10N 2040/25; C10N 2080/00; C07C 319/28; C07C 323/20; B01D 3/40

See application file for complete search history.

(56) References Cited

U.S. PATENT DOCUMENTS

| | | | |
|---|---|---|---|
| 4,123,371 A | 10/1978 | Hori | |
| 5,688,751 A * | 11/1997 | Cleveland | ............ C10M 133/16 508/518 |
| 8,772,209 B2 | 7/2014 | Mahieux et al. | |
| 8,933,002 B2 | 1/2015 | Sinquin et al. | |
| 9,328,309 B2 | 5/2016 | Mahieux et al. | |
| 9,688,939 B1 | 6/2017 | Schwaebisch et al. | |
| 2009/0143264 A1* | 6/2009 | Harrison | ............... C10M 135/30 508/572 |

* cited by examiner

*Primary Examiner* — Vishal V Vasisth

(57) ABSTRACT

Disclosed herein is a process for preparing a sulfurized non-overbased calcium phenate detergent having a reduced content of un-sulfurized alkyl-substituted phenol and its salt. The process steps involve adding an organic solvent to the detergent, wherein the organic solvent has a boiling point of equal or above the boiling point of the un-sulfurized alkyl-substituted phenol. Distilling the organic solvent from the detergent to reduce the content of the un-sulfurized alkyl-substituted phenol.

23 Claims, 2 Drawing Sheets

DISTILLATION PROCESS FOR PRODUCING A LOW TPP PHENATE

This application claims benefit of provisional application No. 62/820,612 filed Mar. 19, 2019

FIELD OF THE INVENTION

The present invention generally relates to processes for preparing detergent compositions. More specifically, the present invention relates to distillation processes for removing un-sulfurized alkyl-substituted phenol and phenate compounds from sulfurized alkyl-substituted phenate detergents.

BACKGROUND OF THE INVENTION

The lubricant additive industry generally uses alkyl phenols (e.g., tetrapropenyl phenol, TPP) to prepare detergents comprising sulfurized metal alkyl phenates. Metal salts of sulfurized alkylphenols are useful lubricating oil additives which impart detergency and dispersancy to the lubricating oil for various engines such as marine, automotive, railroad and air-cooled engines, as well as providing for an alkalinity reserve in the lubricating oil. Alkalinity reserve is generally necessary to neutralize acids generated during operation of the engine. Without this alkalinity reserve, the acids so generated could result in harmful engine corrosion. However, there may be some unreacted alkyl phenols such as tetrapropenyl phenol present in the sulfurized metal alkyl phenate as well as in lubricating oils containing one or more of the sulfurized metal alkyl phenates.

A recent reproductive toxicity study in rats sponsored by the Petroleum Additives Panel of the American Chemistry Council shows that free or unreacted TPP may cause adverse effects on male and female reproductive organs. Further, it is believed that TPP may be corrosive or irritating to the skin.

To reduce any potential health risks and to avoid potential regulatory issues, there is a need to reduce the amount of free unsulfurized alkyl-substituted hydroxyaromatic compound and its metal salt in the salt of a sulfurized alkyl-substituted hydroxyaromatic composition in a simple, cost efficient manner. Although there are ongoing efforts (e.g., U.S. Pat. No. 9,688,939), residual TPP is still a significant technical problem. Accordingly, it is desirable to provide an improved process for preparing a salt of a sulfurized alkyl-substituted hydroxyaromatic composition which has relatively low levels of unsulfurized alkyl-substituted hydroxyaromatic compound and its metal salt.

SUMMARY OF THE INVENTION

In accordance with one embodiment of the present invention, there is provided a process for preparing a sulfurized non-overbased calcium phenate detergent having a reduced content of un-sulfurized alkyl-substituted phenol and the salt thereof, the process comprising the steps of (a) adding an organic solvent to the detergent, wherein the organic solvent has a boiling point equal or above the boiling point of the un-sulfurized alkyl-substituted phenol and (b) distilling the organic solvent from the detergent thereby reducing the content of the un-sulfurized alkyl-substituted phenol.

In accordance with another embodiment of the present invention, there is provided a concentrate composition obtained from distillation of sulfurized alkyl-substituted phenols, the concentrate composition comprising a sulfurized non-overbased calcium phenate that includes an alkyl-substituted group, wherein the alkyl-substituted group is derived from propylene oligomer, wherein the sulfurized non-overbased calcium phenate is substantially free of un-sulfurized phenol or un-sulfurized phenate, wherein the un-sulfurized phenol or a calcium salt thereof is present in less than 0.3 wt % of the concentrate composition at 4.25 wt % or greater of calcium.

In accordance with yet another embodiment of the present invention, there is provided a lubricating oil composition comprising a base oil and a calcium salt of a sulfurized alkyl-substituted compound containing reduced amount of combined mass of an un-sulfurized alkyl-substituted compound and its un-sulfurized calcium salt, the calcium salt of a sulfurized alkyl-substituted compound being produced by the process comprising (a) sulfurizing and neutralizing an alkyl-substituted phenol compound derived from alkylation of a phenol-based compound with one or more olefins comprising a propylene oligomers to provide a calcium salt of the sulfurized alkyl-substituted phenol; (b) adding an organic solvent to the calcium salt of the sulfurized alkyl-substituted phenol from (a), wherein the organic solvent has a boiling point of equal or above the boiling point of the un-sulfurized alkyl-substituted phenol; and (c) distilling the organic solvent away to provide a sulfurized alkyl-substituted phenol compound that is substantially free of the un-sulfurized alkyl-substituted phenol compound, wherein the calcium salt of the sulfurized alkyl-substituted phenol compound contains less than about 0.3% by combined mass of the un-sulfurized alkyl-substituted phenol compound and its un-sulfurized metal salt at 4.25 wt % or greater of calcium.

In accordance with still yet another embodiment of the present invention, there is provided a calcium salt of a sulfurized alkyl-substituted compound containing reduced amount of combined mass of an un-sulfurized alkyl-substituted compound and its un-sulfurized metal salt, the salt of a sulfurized alkyl-substituted compound being produced by the process comprising: (a) sulfurizing and neutralizing an alkyl-substituted phenol compound derived from alkylation of a phenol-based compound with one or more olefins comprising a propylene oligomers to provide a calcium salt of the sulfurized alkyl-substituted phenol; (b) adding an organic solvent to the calcium salt of the sulfurized alkyl-substituted phenol from (a), wherein the organic solvent has a boiling point of equal or above the boiling point of the un-sulfurized alkyl-substituted phenol; and (c) distilling the organic solvent away to provide a sulfurized alkyl-substituted phenol compound that is substantially free of the un-sulfurized alkyl-substituted phenol compound, wherein the calcium salt of the sulfurized alkyl-substituted phenol compound contains less than about 0.3% by combined mass of the un-sulfurized alkyl-substituted phenol compound and its un-sulfurized metal salt at 4.25 wt % or greater of calcium.

DETAILED DESCRIPTION OF THE INVENTION

Figure 1:
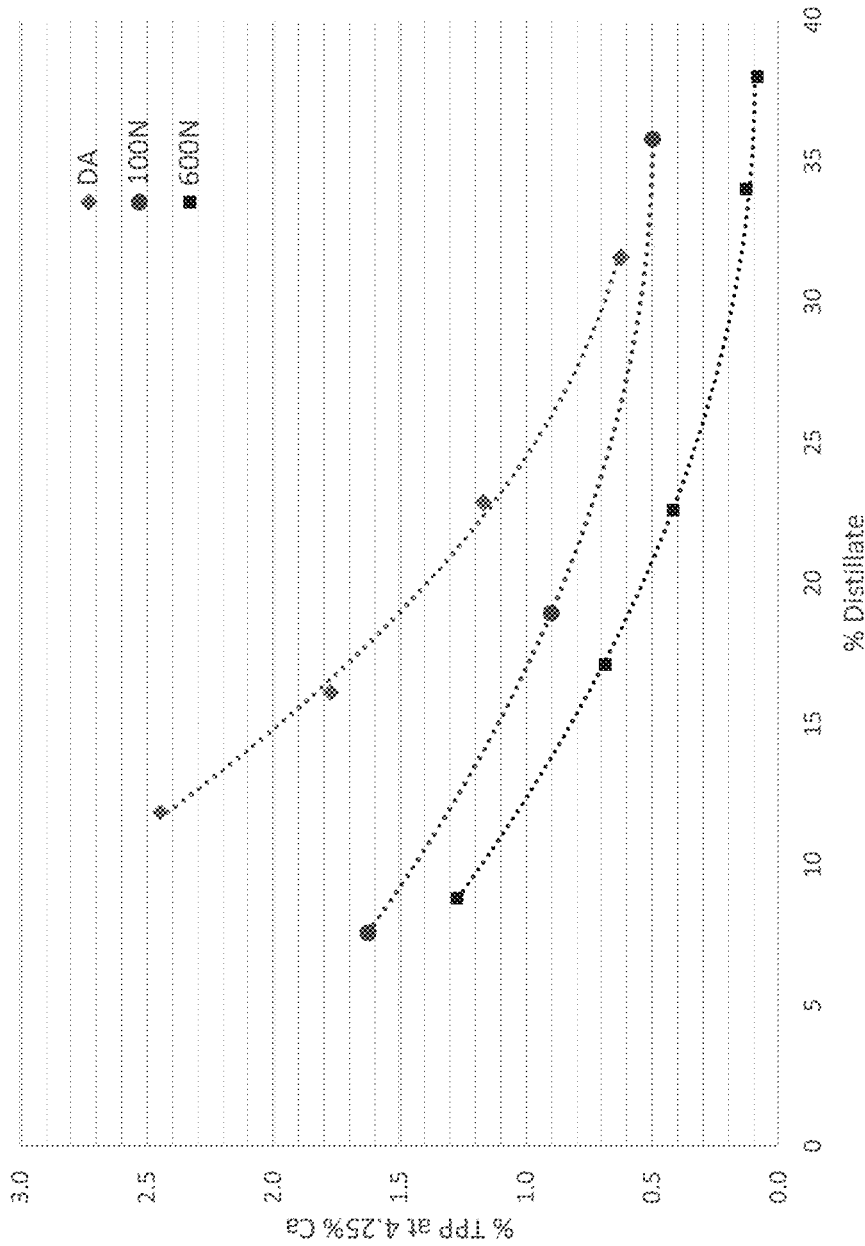
FIG. 1 graphically illustrates and compares the residual TPP levels in a phenate detergent product undergoing a TPP removal distillation step in different organic solvents (decyl alcohol, 100N base oil, or 600N base oil).

The term "phenol" refers to a phenol-based compound, or a salt thereof.

The term "TPP" as used herein refers to tetrapropenyl phenol or a salt thereof.

The term "lime" as used herein refers to calcium hydroxide, also known as slaked lime or hydrated lime.

The term "Total Base Number" or "TBN" as used herein refers to the amount of base equivalent to milligrams of KOH in 1 gram of sample. Thus, higher TBN numbers reflect more alkaline products, and therefore a greater alkalinity reserve. The TBN of a sample can be determined by ASTM Test No. D2896 or any other equivalent procedure.

The present invention is directed to a distillation process for removing unwanted un-sulfurized alkyl-substituted phenols or salts thereof from sulfurized alkyl-substituted phenols after sulfurization reaction. It has been unexpectedly discovered that utilizing a solvent with a relatively high boiling point with non-overbased phenates during the distillation process can greatly enhance removal of the un-sulfurized products. The non-overbased phenates have a TBN ranging from 10-250 in oil-free basis. The starting phenate has a TBN of about 125. Conventional TPP removal has typically focused on using lower boiling point solvents and overbased phenates.

In accordance with the present invention, residual levels of the un-sulfurized products can go down to about 0.3 wt %, 0.2 wt %, or 0.1 wt %, or lower. This is significantly better than some conventional distillation removal methods in which residual levels of un-sulfurized alkyl-substituted phenols and salts thereof can be at least an order of magnitude higher (about 3 wt % to 7 wt %).

Sulfurization of Alkyl-Substituted Phenol

The sulfurized alkyl-substituted phenol can be obtained by sulfurizing an alkyl-substituted phenol in the presence of base to provide a sulfurized alkyl-substituted phenol reaction product. For example, the alkyl-substituted phenol compound is sulfurized by contacting the alkyl-substituted phenol compound with a sulfur source which introduces S, bridging groups between alkyl-substituted phenol compounds, wherein x is 1 to 7 (or more typically 1 or 2). Any suitable sulfur source can be used such as, for example, elemental sulfur or a halide thereof such as sulfur monochloride or sulfur dichloride.

The base catalyzes the reaction to incorporate sulfur onto the alkyl-substituted phenol compound. Suitable base includes, but is not limited to, NaOH, KOH, $Ca(OH)_2$ and the like and mixtures thereof. The base is generally employed at from about 0.01 to about 1 mole percent to the alkyl-substituted phenol compound in the reaction system. Sulfur is generally employed at from about 0.5 to about 4 moles per mole of the alkyl-substituted phenol compound in the reaction system. The temperature range in which the sulfurization reaction is carried out is generally about 150° C. to about 220° C. The reaction can be conducted under atmospheric pressure (or slightly lower) or at elevated pressures.

Neutralization of Sulfurized Alkyl-Substituted Phenol

The sulfurized alkyl-substituted phenol compound is then neutralized to provide a salt of the sulfurized alkyl-substituted phenol compound. Numerous methods are known in the art to neutralize sulfurized alkyl-substituted phenol compound and to produce basic phenates by incorporation of a source of base. In general, neutralization can be carried out by contacting the sulfurized alkyl-substituted phenol compound with a metal base under reactive conditions, to provide a salt of the sulfurized alkyl-substituted phenol compound.

Suitable metal basic compounds include hydroxides, oxides or alkoxides of the metal such as (1) an alkali metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide and aluminum hydroxide. Representative examples of metal basic compounds with oxide functionality include lithium oxide, magnesium oxide, calcium oxide and barium oxide. The alkaline earth metal base can be slaked lime (calcium hydroxide), because of its handling convenience and cost versus, for example, calcium oxide.

Neutralization can be conducted in a suitable solvent or diluents oil, such as toluene, xylene and commonly with a promoter such as an alcohol, e.g., a C1 to C16 alcohol, such as methanol, decyl alcohol, or 2-ethyl hexanol; a diol, e.g., C2 to C4 alkylene glycols, such as ethylene glycol; and/or carboxylic acids. Suitable diluent oils include naphthenic oils and mixed oils, e.g., paraffinic oils such as 100 neutral (100N) oil. The quantity of solvent or diluent oil used is such that the amount of solvent or oil in the final product constitutes from about 25% to about 65% by weight of the final product, or from about 30% to about 50%. For example, the source of alkaline earth metal is added in excess as a slurry (i.e., as a pre-mixture of source of an alkaline earth metal lime, solvent or diluent oil) and then reacted with the sulfurized alkyl-substituted phenol compound.

The neutralization reaction between the metal base and the sulfurized alkyl-substituted phenol compound is typically conducted at temperatures above room temperature (20° C.). The neutralization reaction itself should take place for a period of time from about 5 to about 60 min. If desired, the neutralization reaction is carried out in the presence of a promoter such as ethylene glycol, formic acid, acetic acid, and the like and mixtures thereof. Upon completion of the sulfurization and neutralization steps, reaction mixture is typically heated to 200° C. to 230° C. under vacuum to remove any low boiling solvents used in the process as well as residual water. In some embodiments, the sulfurization and neutralization reactions can take place simultaneously.

Distillation Process for Removing TPP

In accordance with the present invention, TPP can be removed from the sulfurized alkyl-substituted phenates to form a concentrate product. TPP removal is performed via a distillation process to achieve a TPP concentration substantially lower than conventional methods.

The product of the sulfurization and neutralization steps from above can be blended with an organic solvent (e.g., 600 neutral oil or 600N) that has a higher boiling point than the un-sulfurized alkyl-substituted phenol. Other suitable organic solvents include relatively high molecular weight alkylcyclohexanes and alkylbenzenes such as octadecylcyclohexane and octadecylbenzene which have boiling points of 400° C. or greater. The blending will bring the organic solvent concentration to about 10 wt. % to about 30 wt %.

The diluted sulfurized alkyl-substituted phenate is then distilled in a suitable equipment such as a wiped film evaporator (WFE) under appropriate temperatures and pressures. Distillation pressure is typically on the order of 0.1 to 10 mbar with the temperature ranging from 150 to 250° C. depending on the exact WFE pressure.

The higher boiling point organic solvent ensures that some solvent is left in the phenate during this process. This avoids excessively high viscosities as lower boiling point solvents are entirely distilled away. The organic solvent is then distilled from the product to reduce the content of un-sulfurized alkyl substituted phenol and salts thereof.

The resulting salt of a sulfurized alkyl-substituted phenol compound contains less than about 0.3% by combined mass of the un-sulfurized alkyl-substituted phenol compound, its un-sulfurized metal salt and any diluent oil. In one embodiment, a salt of the sulfurized alkyl-substituted phenol compound contains less than about 0.2% by combined mass of the un-sulfurized alkyl-substituted phenol compound and its un-sulfurized metal salt. In one embodiment, a salt of the sulfurized alkyl-substituted phenol compound contains less than about 0.1% by combined mass of the un-sulfurized alkyl-substituted phenol compound and its un-sulfurized metal salt.

Lubricating Oil Composition

Another embodiment of the present invention is directed to a lubricating oil composition containing at least (a) an oil of lubricating viscosity; and (b) at least one salt of a sulfurized alkyl-substituted phenol compound of this invention which is useful as a lubricating oil additive. The lubricating oil compositions can be prepared by admixing, by conventional techniques, an appropriate amount of the lubricating oil additive of this invention with a base oil of lubricating viscosity. The selection of the particular base oil depends on the contemplated application of the lubricant and the presence of other additives. Generally, a salt of a sulfurized alkyl-substituted phenol compound of this invention will be present in the lubricating oil compositions in an amount of about amount of about 0.01 to about 40 wt. %, based on the total weight of the lubricating oil composition. In one embodiment, a salt of a sulfurized alkyl-substituted phenol compound of this invention will be present in the lubricating oil compositions in an amount of from about 0.1 to about 20 wt. %, based on the total weight of the lubricating oil composition.

The oil of lubricating viscosity for use in the lubricating oil compositions of this invention, also referred to as a base oil, can be present an amount of about 50 wt % or less, greater than 50 wt %, preferably greater than about 70 wt %, more preferably from about 80 to about 99.5 wt % and most preferably from about 85 to about 98 wt %, based on the total weight of the composition. Additionally, the base oils can optionally contain viscosity index improvers, e.g., polymeric alkylmethacrylates; olefinic copolymers, e.g., an ethylene-propylene copolymer or a styrene-butadiene copolymer; and the like and mixtures thereof.

The viscosity of the base oil is dependent upon the application. Accordingly, the viscosity of a base oil for use herein will ordinarily range from about 2 to about 2000 centistokes (cSt) at 100° Centigrade (° C.). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-8, 0W-16, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

The oil of lubricating viscosity (sometimes referred to as "base stock" or "base oil") is the primary liquid constituent of a lubricant, into which additives and possibly other oils are blended, for example to produce a final lubricant (or lubricant composition). A base oil, which is useful for making concentrates as well as for making lubricating oil compositions therefrom, may be selected from natural (vegetable, animal or mineral) and synthetic lubricating oils and mixtures thereof.

Definitions for the base stocks and base oils in this disclosure are the same as those found in American Petroleum Institute (API) Publication 1509 Annex E ("API Base Oil Interchangeability Guidelines for Passenger Car Motor Oils and Diesel Engine Oils," December 2016). Group I base stocks contain less than 90% saturates and/or greater than 0.03% sulfur and have a viscosity index greater than or equal to 80 and less than 120. Group II base stocks contain greater than or equal to 90% saturates and less than or equal to 0.03% sulfur and have a viscosity index greater than or equal to 80 and less than 120. Group III base stocks contain greater than or equal to 90% saturates and less than or equal to 0.03% sulfur and have a viscosity index greater than or equal to 120. Group IV base stocks are polyalphaolefins (PAO). Group V base stocks include all other base stocks not included in Group I, II, III, or IV.

Natural oils include animal oils, vegetable oils (e.g., castor oil and lard oil), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful. Natural oils vary also as to the method used for their production and purification, for example, their distillation range and whether they are straight run or cracked, hydrorefined, or solvent extracted.

Synthetic oils include hydrocarbon oil. Hydrocarbon oils include oils such as polymerized and interpolymerized olefins (e.g., polybutylenes, polypropylenes, propylene isobutylene copolymers, ethylene-olefin copolymers, and ethylene-alphaolefin copolymers). Polyalphaolefin (PAO) oil base stocks are commonly used synthetic hydrocarbon oil. By way of example, PAOs derived from C8 to C14 olefins, e.g., C8, C10, C12, C14 olefins or mixtures thereof, may be utilized.

Other useful fluids for use as base oils include non-conventional or unconventional base stocks that have been processed, preferably catalytically, or synthesized to provide high performance characteristics.

Non-conventional or unconventional base stocks/base oils include one or more of a mixture of base stock(s) derived from one or more Gas-to-Liquids (GTL) materials, as well as isomerate/isodewaxate base stock(s) derived from natural wax or waxy feeds, mineral and or non-mineral oil waxy feed stocks such as slack waxes, natural waxes, and waxy stocks such as gas oils, waxy fuels hydrocracker bottoms, waxy raffinate, hydrocrackate, thermal crackates, or other mineral, mineral oil, or even non-petroleum oil derived waxy materials such as waxy materials received from coal liquefaction or shale oil, and mixtures of such base stocks.

Base oils for use in the lubricating oil compositions of present disclosure are any of the variety of oils corresponding to API Group I, Group II, Group III, Group IV, and Group V oils, and mixtures thereof, preferably API Group II, Group III, Group IV, and Group V oils, and mixtures thereof, more preferably the Group III to Group V base oils due to their exceptional volatility, stability, viscometric and cleanliness features.

Typically, the base oil will have a kinematic viscosity at 100° C. (ASTM D445) in a range of 2.5 to 20 mm2/s (e.g., 3 to 12 mm2/s, 4 to 10 mm2/s, or 4.5 to 8 mm2/s).

The present lubricating oil compositions may also contain conventional lubricant additives for imparting auxiliary functions to give a finished lubricating oil composition in which these additives are dispersed or dissolved. For example, the lubricating oil compositions can be blended with antioxidants, ashless dispersants, anti-wear agents, detergents such as metal detergents, rust inhibitors, dehazing agents, demulsifying agents, friction modifiers, metal deactivating agents, pour point depressants, viscosity modifiers, antifoaming agents, co-solvents, package compatibilizers, corrosion-inhibitors, dyes, extreme pressure agents and the like and mixtures thereof. A variety of the additives are known and commercially available. These additives, or their analogous compounds, can be employed for the preparation of the lubricating oil compositions of the invention by the usual blending procedures.

Each of the foregoing additives, when used, is used at a functionally effective amount to impart the desired properties to the lubricant. Thus, for example, if an additive is an ashless dispersant, a functionally effective amount of this ashless dispersant would be an amount sufficient to impart the desired dispersancy characteristics to the lubricant. Generally, the concentration of each of these additives, when used, may range, unless otherwise specified, from about 0.001 to about 20 wt. %, such as about 0.01 to about 10 wt. %.

EXAMPLES

The following non-limiting examples are illustrative of the present invention. For 600N (a base oil) samples, the follow protocol was used.

The phenate detergent, with a starting TPP content of 3.8% at 4.25% calcium, was blended with 600N. Sufficient 600N was added to reach a concentration of 17 wt %. The 600N was used as a processing aid as the 100N used in phenate production also distills at typical distillation conditions whereas 600N does not. Use of 600N ensures that some oil is left in the phenate to avoid excessively high viscosities as the alkylphenol and 100N codistill from the phenate detergent. Both TPP and calcium concentrations were measured for the distilled product. TPP concentrations were corrected to 4.25 wt % calcium content level. Details of how to measure TPP content can be found in U.S. Pat. Nos. 8,772,209 and 9,328,309, which are hereby incorporated by reference.

Example 1

Table 1 summarizes atmospheric boiling point data for various organic solvents including isodecanol (DA), neutral oil 100N, neutral oil 600N, as well as TPP. The 5% and 95% boiling point data in Table 1 were determined by ASTM 7169 (simulated distillation by gas chromatography). As shown, the boiling point ranges generally trend from DA which has the lowest range to 600N which has the highest range. DA boils at a lower temperature than TPP, while 600N has a higher boiling point range.

TABLE 1

| ASTM 7169 Boiling Points for Organic Solvents | | |
|---|---|---|
| Solvent | 5% Boiling Point | 95% Boiling Point |
| Decanol | 210° C. | 240° C. |
| TPP | 310° C. | 370° C. |
| 100N Oil | 335° C. | 465° C. |
| 600N Oil | 430° C. | 569° C. |

FIG. 1 illustrates the effect of organic solvent on the amount of residual TPP present during progress of a TPP removal distillation step. There will be some levels of 100N in the 600N sample as 100N is used during sulfurization and/or neutralization steps. 600N was added post-sulfurization/neutralization and acts as a co-solvent with existing 100N. As shown, 600N (highest boiling point solvent) can achieve the lowest residual TPP level (down to about 0.1 wt % or lower). In terms of TPP removal, 600N worked best, followed by 100N and isodecanol.

Example 2

Figure 2:
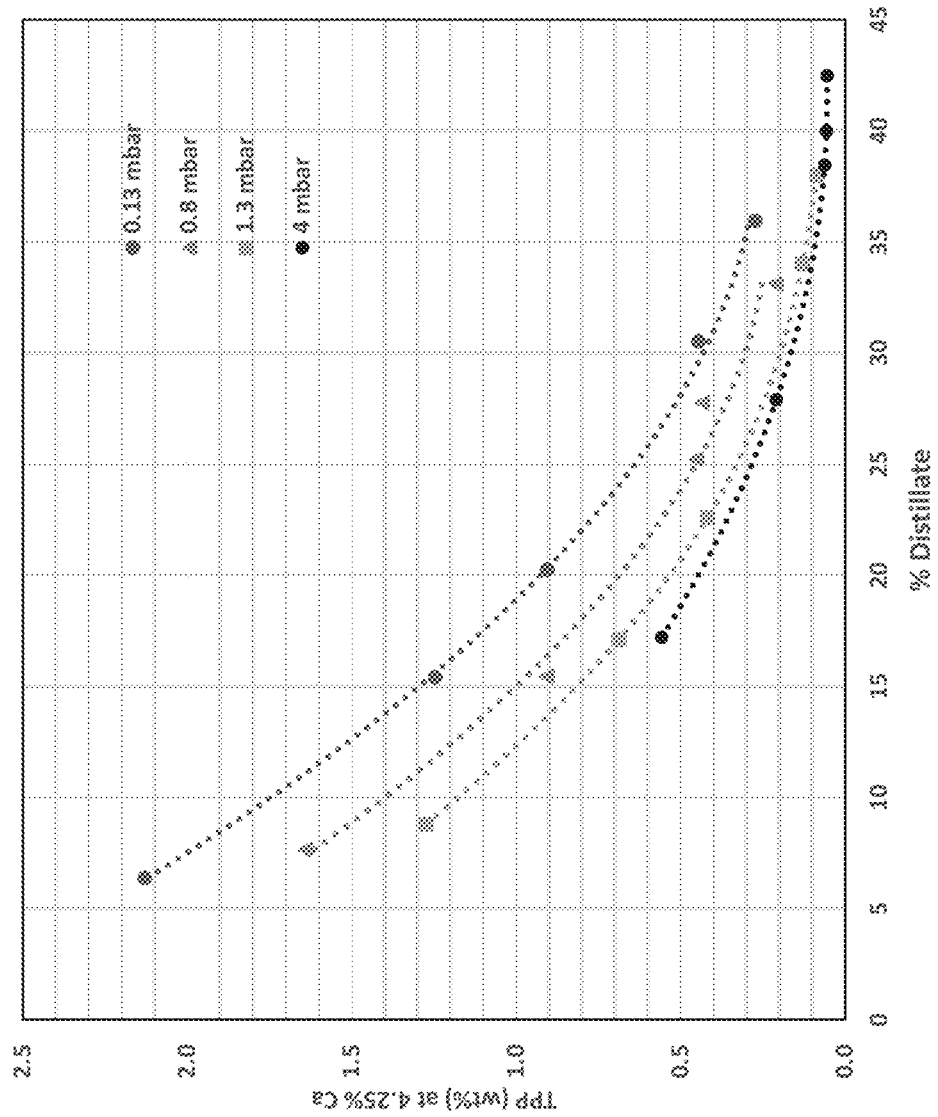
FIG. 2 graphically illustrates and compares the residual TPP levels in a phenate detergent product undergoing a TPP removal distillation step using 600N solvent at various pressures (0.13 to 4 mbar).

This example illustrates the effect of pressure on TPP removal during the progress of a TPP removal distillation step. In this example, 600N was used as the organic solvent. Four different pressures were tested: 0.13 mbar, 0.8 mbar, 1.3 mbar, and 4 mbar. As shown in FIG. 2, lower TPP levels were achieved under higher pressures. TPP was reduced by over a factor of 10 at the higher pressures as level of distillation increased beyond 20%. Somewhat surprisingly, lower pressures were not preferred.

What is claimed is:

1. A process for preparing a sulfurized non-overbased calcium phenate detergent having a reduced content of un-sulfurized alkyl-substituted phenol and the salt thereof, the process comprising the steps of:
    (a) adding an organic solvent to the detergent, wherein the organic solvent has a boiling point of equal or above the boiling point of the un-sulfurized alkyl-substituted phenol; and
    (b) distilling the organic solvent from the detergent thereby reducing the content of the un-sulfurized alkyl-substituted phenol.

2. The process of claim 1, wherein the sulfurized non-overbased calcium phenate detergent is an alkyl-substituted phenate.

3. The process of claim 2, wherein the alkyl-substituted phenate has an alkyl group ranging from 9 and 18 carbons in length.

4. The process of claim 2, wherein the alkyl-substituted phenate has been alkylated by a propylene or a butylene oligomer.

5. The process of claim 4, wherein the propylene or butylene oligomer is a tetramer.

6. The process of claim 1, wherein the organic solvent is neutral oil 600.

7. The process of claim 1, wherein the distilling occurs at 1 mbar or greater.

8. The process of claim 1, wherein the detergent has been neutralized in presence of a promoter.

9. The process of claim 8, wherein the promoter is an alcohol, a diol, or a carboxylic acid.

10. A concentrate composition obtained from distillation of sulfurized alkyl-substituted phenols, the concentrate composition comprising:

a sulfurized non-overbased calcium phenate that includes an alkyl-substituted group, wherein the alkyl-substituted group is derived from propylene oligomer, wherein the sulfurized non-overbased calcium phenate is substantially free of un-sulfurized phenol or un-sulfurized phenate, wherein the un-sulfurized phenol or a calcium salt thereof is present in less than 0.3 wt % of the concentrate composition at 4.25 wt % or greater of calcium.

11. The concentrate composition of claim 10, wherein the un-sulfurized phenol or un-sulfurized phenate are present in less than 0.2 wt. % of the concentrate composition.

12. The concentrate composition of claim 10, wherein the un-sulfurized phenol or un-sulfurized phenate are present in less than 0.1 wt. % of the concentrate composition.

13. The concentrate composition of claim 10, wherein the propylene oligomer is propylene tetramer.

14. The concentrate composition of claim 10, wherein the sulfurized non-overbased calcium phenate include one or more sulfur linkages.

15. The concentrate composition of claim 14, wherein the one or more sulfur linkages is between an average of 1 to 7 sulfur atoms.

16. The concentrate composition of claim 10, wherein the non-overbased calcium phenate has a TBN ranging from 10 to 250 in oil-free basis.

17. A lubricating oil composition comprising:
a base oil; and
a calcium salt of a sulfurized alkyl-substituted compound containing reduced amount of combined mass of an un-sulfurized alkyl-substituted compound and its un-sulfurized calcium salt, the calcium salt of a sulfurized alkyl-substituted compound being produced by the process comprising:
(a) sulfurizing and neutralizing an alkyl-substituted phenol compound derived from alkylation of a phenol-based compound with one or more olefins comprising a propylene oligomers to provide a calcium salt of the sulfurized alkyl-substituted phenol;
(b) adding an organic solvent to the calcium salt of the sulfurized alkyl-substituted phenol from (a), wherein the organic solvent has a boiling point of equal or above the boiling point of the un-sulfurized alkyl-substituted phenol; and
(c) distilling the organic solvent away to provide a sulfurized alkyl-substituted phenol compound that is substantially free of the un-sulfurized alkyl-substituted phenol compound, wherein the calcium salt of the sulfurized alkyl-substituted phenol compound contains less than about 0.3% by combined mass of the un-sulfurized alkyl-substituted phenol compound and its un-sulfurized metal salt at 4.25 wt % or greater of calcium.

18. The lubricating oil composition of claim 17, further comprising:
an antioxidant, a dispersant, an anti-wear agent, a detergent, a rust inhibitor, a dehazing agent, a demulsifying agent, a friction modifier, a metal deactivating agent, a pour point depressant, a viscosity modifier, an anti-foaming agent, a co-solvent, a package compatibilizer, a corrosion-inhibitor, a dye, or an extreme pressure agent.

19. A calcium salt of a sulfurized alkyl-substituted compound containing reduced amount of combined mass of an un-sulfurized alkyl-substituted compound and its un-sulfurized metal salt, the salt of a sulfurized alkyl-substituted compound being produced by the process comprising:
(a) sulfurizing and neutralizing an alkyl-substituted phenol compound derived from alkylation of a phenol-based compound with one or more olefins derived from a propylene oligomers to provide a calcium salt of the sulfurized alkyl-substituted phenol;
(b) adding an organic solvent to the calcium salt of the sulfurized alkyl-substituted phenol from (a), wherein the organic solvent has a boiling point of equal or above the boiling point of the un-sulfurized alkyl-substituted phenol; and
(c) distilling the organic solvent away to provide a sulfurized alkyl-substituted phenol compound that is substantially free of the un-sulfurized alkyl-substituted phenol compound, wherein the calcium salt of the sulfurized alkyl-substituted phenol compound contains less than about 0.3% by combined mass of the un-sulfurized alkyl-substituted phenol compound and its un-sulfurized metal salt at 4.25 wt % or greater of calcium.

20. The salt of a sulfurized alkyl-substituted phenol compound of claim 19, wherein the propylene oligomer is a propylene tetramer.

21. The salt of a sulfurized alkyl-substituted phenol compound of claim 19, wherein the salt of the sulfurized alkyl-substituted phenol compound contains less than about 0.2% by combined mass of the un-sulfurized alkyl-substituted phenol compound and its un-sulfurized metal salt.

22. The salt of a sulfurized alkyl-substituted phenol compound of claim 19, wherein the salt of the sulfurized alkyl-substituted phenol compound contains less than about 0.1% by combined mass of the un-sulfurized alkyl-substituted phenol compound and its un-sulfurized metal salt.

23. The concentrate composition of claim 10, wherein the un-sulfurized phenol or un-sulfurized phenate are present in less than 0.15 wt. % of the concentrate composition.

* * * * *